US009554748B2

(12) United States Patent
Banet et al.

(10) Patent No.: US 9,554,748 B2
(45) Date of Patent: Jan. 31, 2017

(54) SYSTEM FOR MONITORING HEART FAILURE PATIENTS FEATURING NECKLACE-SHAPED SENSOR AND DISPLAY BASED ON A CONVENTIONAL TELEVISION OR MOBILE DEVICE

(71) Applicant: TOSENSE, INC., La Jolla, CA (US)

(72) Inventors: Matthew Banet, San Diego, CA (US); Susan Meeks Pede, Encinitas, CA (US); Marshal Singh Dhillon, San Diego, CA (US)

(73) Assignee: TOSENSE, INC., La Jolla, CA (US)

( * ) Notice: Subject to any disclaimer, the term of this patent is extended or adjusted under 35 U.S.C. 154(b) by 341 days.

(21) Appl. No.: 14/267,588

(22) Filed: May 1, 2014

(65) Prior Publication Data

US 2014/0330090 A1 Nov. 6, 2014

Related U.S. Application Data

(60) Provisional application No. 61/818,162, filed on May 1, 2013.

(51) Int. Cl.
*A61B 5/00* (2006.01)
*A61B 5/0205* (2006.01)
(Continued)

(52) U.S. Cl.
CPC ........... *A61B 5/6822* (2013.01); *A61B 5/0205* (2013.01); *A61B 5/02028* (2013.01);
(Continued)

(58) Field of Classification Search
CPC ... A61B 5/002; A61B 5/02028; A61B 5/0205; A61B 5/02055; A61B 5/04085; A61B 5/0452; A61B 5/0537; A61B 5/1118; A61B 5/6822; A61B 5/721; A61B 5/7235; A61B 5/7435
See application file for complete search history.

(56) References Cited

U.S. PATENT DOCUMENTS

2011/0066062 A1 3/2011 Banet et al.

OTHER PUBLICATIONS

Bernstein, Impedance cardiography: Pulsatile blood flow and the biophysical and electrodynamic basis for the stroke volume equations. J Electr Bioimp; 2010;1:2-17.
(Continued)

*Primary Examiner* — Amanda Patton
(74) *Attorney, Agent, or Firm* — Acuity Law Group, PC; Michael A. Whittaker

(57) ABSTRACT

The invention provides a system for monitoring a patient that includes a sensor configured to drape around the patient's neck. The sensor features an impedance sensor for measuring fluids, an ECG sensor for measuring cardiac activity, and a first wireless transceiver for transmitting this information. Integrated with the sensor is a computer, featuring a second wireless transceiver, video output system, and a computer processing unit (CPU). The CPU is configured to receive control signals from the first wireless transceiver that control a software program and the information related to fluids and cardiac activity. The software program renders a graphical user interface that displays the information through the video output system. The system also includes a conventional television set or mobile device that interfaces to the computer through the video output system and renders the graphical user interface.

19 Claims, 10 Drawing Sheets

(51) Int. Cl.
     *A61B 5/0452*     (2006.01)
     *A61B 5/02*       (2006.01)
     *A61B 5/0408*     (2006.01)
     *A61B 5/053*      (2006.01)
     *A61B 5/11*       (2006.01)

(52) U.S. Cl.
     CPC ........ *A61B 5/0452* (2013.01); *A61B 5/04085* (2013.01); *A61B 5/0537* (2013.01); *A61B 5/7435* (2013.01); *A61B 5/002* (2013.01); *A61B 5/02055* (2013.01); *A61B 5/1118* (2013.01); *A61B 5/721* (2013.01); *A61B 5/7235* (2013.01)

(56) References Cited

OTHER PUBLICATIONS

Bromley et al., Physiological range of peak cardiac power output in healthy adults. Clin Physiol Funct Imaging. Jul. 2006;26(4):240-246.

Harley et al., Pressure-Flow Studies in Man. An Evaluation of the Duration of the Phases of Systole. J Clin Invest. May 1969;48(5):895-905.

Jacques et al., Pulse pressure variation and stroke volume variation during increased intra-abdominal pressure: an experimental study. Crit Care. 2011;15(1):R33 (9 pages).

Pina et al., Exercise and Heart Failure: A Statement From the American Heart Association Committee on Exercise, Rehabilitation, and Prevention. Circulation. Mar. 4, 2003;107(8):1210-1225.

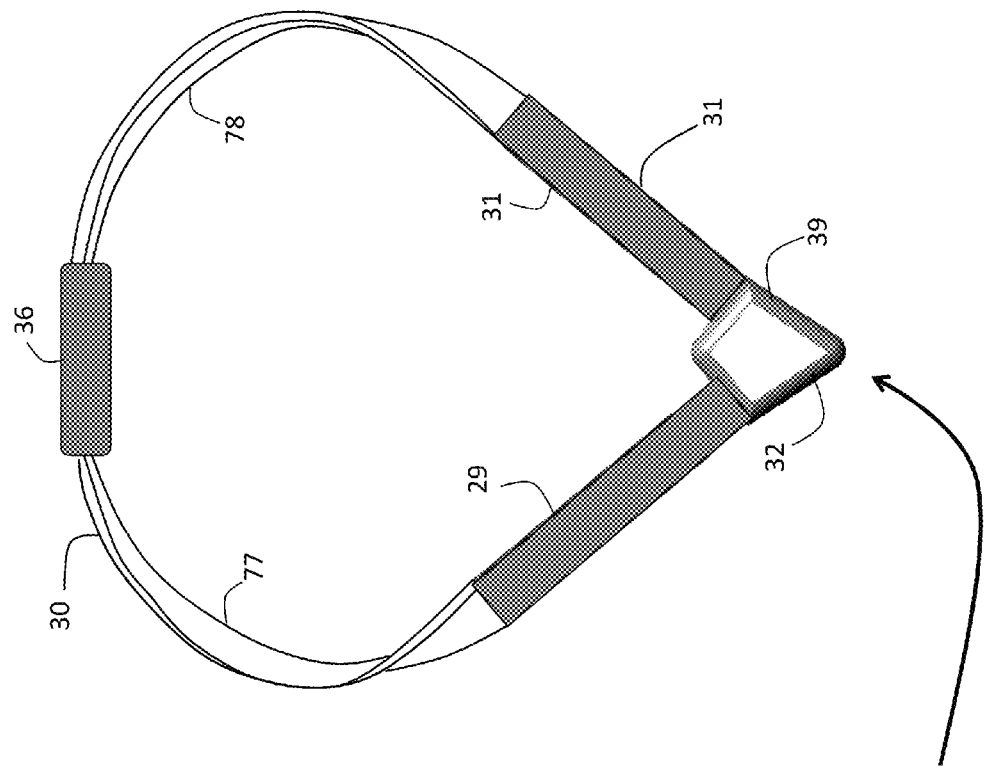
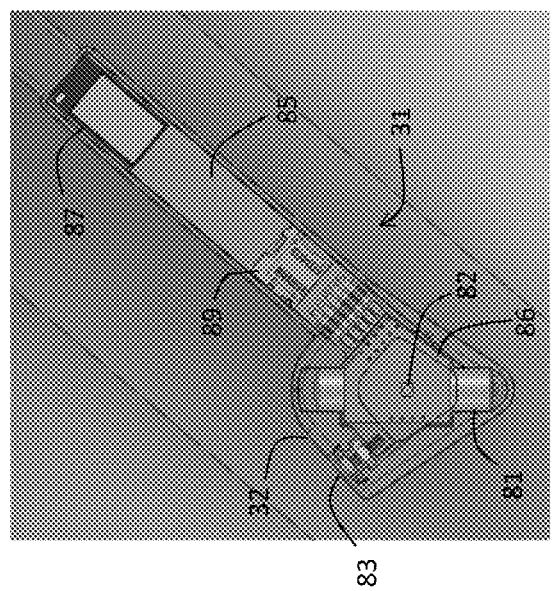
FIG. 4

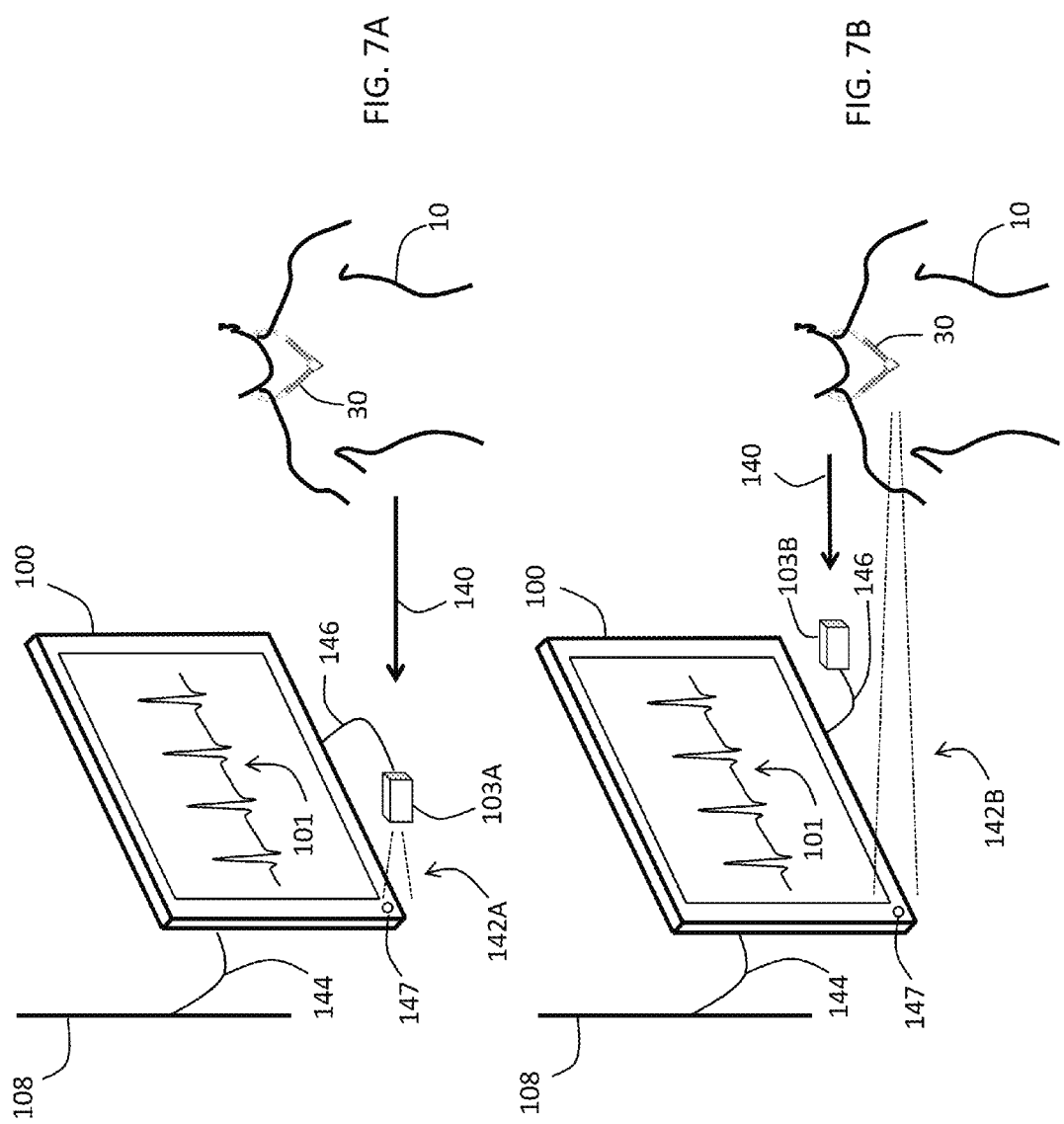

SYSTEM FOR MONITORING HEART FAILURE PATIENTS FEATURING NECKLACE-SHAPED SENSOR AND DISPLAY BASED ON A CONVENTIONAL TELEVISION OR MOBILE DEVICE

CROSS REFERENCES TO RELATED APPLICATIONS

This application claims the benefit of U.S. Provisional Application No. 61/818,162, filed May 1, 2013, which is hereby incorporated in its entirety including all tables, figures, and claims.

STATEMENT REGARDING FEDERALLY SPONSORED RESEARCH OR DEVELOPMENT

None.

BACKGROUND OF THE INVENTION

Field of the Invention

The present invention relates to sensors that measure physiological signals from patients, particularly patients with congestive heart failure (CHF).

Description of the Related Art

Medical devices can measure time-dependent electrocardiograms (ECG) and thoracic bioimpedance (TBI) waveforms from patients. Such devices typically connect to disposable electrodes that adhere to the patient's skin and measure bioelectric signals. Analog circuits within the device process the bioelectric signals to generate the waveform, which with further analysis yields parameters such as heart rate (HR), thoracic fluid levels, stroke volume (SV), cardiac output (CO), and respiratory rate (RR). Other systems within the medical devices measure vital signs such as pulse oximetry (SpO2), pulse rate (PR), and temperature (TEMP). Typically the medical device is remote from the patient, and connects to a body-worn sensor through a cable. Adhesive electrodes are sensors that measure ECG and TBI waveform; these are typically worn on the patient's chest or legs. Patients can wear an optical sensor on their fingers or ear to measure photoplethysmogram (PPG) waveforms, which are then processed to yield SpO2 and PR. TEMP is typically measured with a thermometer inserted in the patient's mouth.

Devices that measure ECG and TBI waveforms are often used to characterize patients suffering from CHF. This condition occurs when the patient's heart is unable to sufficiently pump and distribute blood to meet their body's needs. CHF is typically preceded by an increase of fluid in the thoracic cavity, and can be characterized by shortness of breath, swelling of the legs and other appendages, and intolerance to exercise. It affects nearly 5.3M Americans and has an accompanying cost of somewhere between $30-50B, with roughly $17B attributed to hospital readmissions. Such events are particularly expensive to hospitals, as readmissions occurring within a 30-day period may not reimbursable by Medicare or private insurance as of October 2012, or alternatively may be accompanied by a financial penalty to the hospital.

CHF can also be characterized using Doppler/ultrasound, which measures parameters such as SV, CO, and ejection fraction (EF). Gradual weight gain measured with a simple scale is another method used to indicate CHF in the home environment. However, this parameter is typically not sensitive enough to detect the early onset of CHF, a particularly important time when the condition may be ameliorated by a change in medication or diet.

SV is the mathematical difference between left ventricular end-diastolic volume (EDV) and end-systolic volume (ESV), and represents the volume of blood ejected by the left ventricle with each heartbeat; a typical value is about 80 mL. EF relates to EDV and ESV as described below in Eq. 1, with a typical value for healthy individuals being about 50-65%, and an ejection fraction of less than 40% indicating systolic heart failure.

$$EF = \frac{SV}{EDV} \qquad (1)$$
$$= \frac{EDV - ESV}{EDV}$$

CO is the average, time-dependent volume of blood ejected from the left ventricle into the aorta and, informally, indicates how efficiently a patient's heart pumps blood through their arterial tree; a typical value is about 5 L/min. CO is the product of HR and SV, i.e.:

$$CO = SV \times HR \qquad (2)$$

CHF patients, in particular those suffering from systolic heart failure, may receive implanted devices, such as pacemakers and/or implantable cardioverter-defibrillators, to increase EF and subsequent blood flow throughout the body. These devices also include technologies called 'OptiVol' (from Medtronic) or 'CorVue' (St. Jude) that use circuitry and algorithms within the implanted device to measure the electrical impedance between different leads of the pacemaker. As thoracic fluid increases in the CHF patient, the impedance typically is reduced. Thus this parameter, when read by an interrogating device placed outside the patient's body, can indicate the onset of heart failure.

Corventis Inc. has developed the AVIVO Mobile Patient Management (MPM) System to characterize ambulatory CHF patients. AVIVO is typically used over a 7-day period, during which it provides continual insight into a patient's physiological status by steadily collecting data and wirelessly transmitting it through a small handheld device to a central server for analysis and review. The system consists of three parts: 1) The PiiX sensor, a patient-worn adhesive device that resembles a large (approximately 15" long) bandage and measures fluid status, ECG waveforms, HR, RR, patient activity, and posture; 2) The zLink Mobile Transmitter, a small, handheld device that receives information from the Piix sensor and then transmits data wirelessly to a remote server via cellular technology; and 3) the Corventis Monitoring Center, where data are collected and analyzed. Technicians staff the Monitoring Center, review the incoming data, and in response generate clinical reports made available to prescribing physicians by way of a web-based user interface.

In some cases, physicians can prescribe ambulatory cardiac monitors to CHF patients. These systems measure time-dependent ECG waveforms, from which HR and information related to arrhythmias and other cardiac properties are extracted. They characterize ambulatory patients over short periods (e.g. 24-48 hours) using 'holier' monitors, or over longer periods (e.g. 1-3 weeks) using cardiac event monitors. Conventional holter or event monitors typically include a collection of chest-worn ECG electrodes (typically 3 or 5), an ECG circuit that collects analog signals from the ECG electrodes and converts these into multi-lead ECG waveforms; a processing unit then analyzes the ECG waveforms to determine cardiac information. Typically the patient wears the entire system on their body. Some modern ECG-monitoring systems include wireless capabilities that transmit ECG waveforms and other numerical data through a cellular interface to an Internet-based system, where they are further analyzed to generate, for example, reports describing the patient's cardiac rhythm. In less sophisticated systems, the ECG monitoring system is worn by the patient, and then returned to a company that downloads all relevant information into a computer, which then analyzes it to generate the report. The report, for example, may be imported into the patient's electronic medical record (EMR). The EMR avails the report to cardiologists or other clinicians, who then use it to help characterize the patient.

SUMMARY OF THE INVENTION

The invention features a body-worn sensor, most preferably shaped like a conventional necklace, that measures a collection of physiological parameters and sends them to a computer interfaced with conventional consumer devices, such as a television or mobile device (e.g. mobile telephone or tablet computer). The computer renders the information on a display associated with the device. Preferably, the computer renders a graphical user interface, much like that used in conventional video games, to display the information. The graphical user interface can also display other content (e.g. videos or animations) that guide the patient through pre-determined exercise routines while simultaneously collecting their physiological information. In this way, the invention can collect physiological information under consistent conditions, thereby allowing the patient and outside observers of the information (e.g. family members, clinicians) to estimate the patient's progress towards a relatively healthy state. Perhaps more importantly, the system can potentially motivate the patient to regularly perform exercise, thereby improving their condition.

The sensor measures all of the above-mentioned properties while featuring a comfortable, easy-to-wear form factor that resembles a piece of conventional jewelry. It is lightweight (about 100 grams) and designed to resemble something other than a conventional medical device. During use, it simply drapes around the neck, where it is held in place by a pair of customized electrodes that measure physiological signals, described in more detail below.

The sensor measures ECG and TBI waveforms using electrical circuitry disposed in the strands that hold it in place. On a bottom surface of the sensor is a pair of customized electrode holders that connects through a magnetic field to a mated set of magnets in a custom electrode. The electrodes contain three separate electrode regions to measure ECG and TBI waveforms. The electrode holders magnetically hold the electrodes in place while providing the necessary electrical couplings. Prior to a measurement, the electrodes are simply held proximal to the electrode holders. Magnetic fields between these components cause the electrodes to easily snap into place, after which the measurement is made. Additionally, the magnets providing the magnetic interface also include a conductive metal coating, meaning they conduct electrical signals sensed by the electrodes into the TBI and ECG analog circuits.

Upper electrodes in each electrode holder supply a drive current for the TBI measurement, while lower electrodes measure a voltage representing the product of the injected drive current and internal impedance in the patient's thoracic cavity. The TBI analog circuit generates an analog TBI waveform, which is then sent to an analog-to-digital converter for digitization. The middle electrode in each of the three-part electrodes measure signals that pass to an ECG circuit within the sensor, where they are processed with a differential amplifier to generate an analog ECG waveform, which is then sent to the analog-to-digital converter for digitization. Once digitized, both the TBI and ECG waveforms are processed as described below to determine both vital signs and hemodynamic parameters.

Strands disposed on both the left and right-hand sides of the patient's neck feature both analog and digital circuitry. This circuitry, which is typically disposed on non-flexible fiberglass circuit boards, is connected with flexible circuitry embedded in thin, Kapton films. Typically both the flexible and non-flexible circuits are embedded in a soft, silicone rubber film. Alternating non-flexible and flexible circuitry provides the necklace with all the necessary electronics while allowing it to remain flexible and comfortably bend around the patient's neck.

The sensor's form factor is designed for comfort and ease of use, with the ultimate goal of improving patient compliance so that the above-mentioned parameters can be measured in a continuous manner and on a day-to-day basis. The system is targeted for elderly, at-home patients, e.g. those suffering from chronic conditions such as CHF, diabetes, and chronic obstructive pulmonary disease (COPD). It is worn around the patient's neck, a location that is unobtrusive, comfortable, removed from the hands, and able to bear the weight of the sensor without being noticeable to the patient. The neck and thoracic cavity are also relatively free of motion compared to appendages such as the hands and fingers, and thus a sensor affixed to this location minimizes motion-related artifacts. Moreover, motion detectors within the sensor can compensate for motion artifacts, to some degree.

The sensor also features other components that simplify it and improve ease of use. For example, it includes a Bluetooth transmitter that sends data (e.g. waveforms and numerical values) to a remote viewing device associated with a television or mobile device. From there, the data can be forwarded through an Internet-accessible website to a physician for further review. Electrodes and associated electrode holders include mated magnets so that, prior to a measurement, the electrodes simply 'snap' into place, thus eliminating the need for cumbersome snaps and rivets that can be difficult for elderly patients to connect. A battery housed in a bottom portion of the necklace (i.e., where an amulet would connect to a conventional necklace) can be easily replaced without removing the sensor from the patient. In this manner, a fresh battery can be installed when the original battery begins to run low on power, thus allowing the sensor to be used continuously for extended periods of time (e.g. for patient monitoring in a hospital or nursing home).

In one embodiment, the sensor measures pulse arrival time (PAT), which correlates inversely with both SBP and DPB. It is calculated from a time difference between the maximum of the ECG waveform (called the QRS complex), and a fiducial point on the TBI waveform (e.g. the onset of the waveform, or the point of maximum slope, as determined from the maximum of the mathematical derivative). Once determined, the inverse of PAT can be used with a calibration measurement (e.g. one performed with a conventional cuff-based blood pressure monitor) to estimate SBP/DBP. Alternatively, the un-calibrated value of PAT can be used to estimate trends in SBP and DPB.

It is well know that pulse pressure (PP) correlates with SV, and typically this correlation is defined by a single, linear relationship that extends across all patients. Additionally, changes in SV correlate extremely well with changes in PP. Thus, TBI-determined SV yields an independent measurement of PP, and this in turn can increase the measurement accuracy of SBP and DBP.

In general, in one aspect, the invention provides a system for monitoring a patient that includes a sensor configured to drape around the patient's neck. The sensor features an impedance sensor for measuring fluids, an ECG sensor for measuring cardiac activity, and a first wireless transceiver for transmitting information related to fluids and cardiac activity. Integrated with the sensor is a computer, featuring a second wireless transceiver, video output system, and a computer processing unit (CPU). The CPU is configured to receive control signals from the first wireless transceiver that control a software program and the information related to fluids and cardiac activity. The software program renders a graphical user interface that displays the information through the video output system. The system also includes a conventional television set or mobile device that interfaces to the computer through the video output system and renders the graphical user interface.

In embodiments, the sensor is configured to send control signals to the CPU to activate the software program. For example, the control signals can power on the CPU and activate IO pins in the CPU. The CPU, in turn, can operate a second software program that automatically launches the graphical user interface on the television. For example, the CPU can automatically launch the software program at a pre-determined time, or when it detects that the patient has been watching television for a pre-determined period of time.

In other embodiments, the sensor can include a motion sensor, such as an accelerometer. In this case, the CPU can operate a second software program that launches the graphical user interface when the motion sensor detects that the patient is relatively sedentary, or alternatively when the motion sensor detects that the patient is in motion.

In embodiments, the CPU launches the graphical user interface so that it is displayed simultaneously with television programming, e.g. in a picture-in-picture mode with television programming.

In embodiments, the ECG sensor measures a HR or HR variability from the patient, and the CPU launches the graphical user interface when these parameters exceed a predetermined value. In other embodiments, the impedance sensor measures a RR, SV, or fluid level from the patient, and the CPU launches the graphical user interface when these parameters exceed a predetermined value.

In another aspect, the invention provides the above-described sensor, coupled with a computer rendering a graphical user interface that guides the patient through a pre-determined exercise routine, and ports information measured by the sensor through the video output system so it is displayed on a video display.

In another aspect, the invention couples the above-mentioned system with an Internet-based system that receives further information related to the physiological and exercise information through an Internet connection, and displays the information on a website that includes a first interface specific for the patient, and a second interface specific for multiple users other than the patient (e.g. their clinician or family members).

In embodiments, the graphical user interface features a video (either animated or filmed with human actors) that instructs the patient on how to perform the pre-determined exercise routine. The instructions can tell the patient to take a number of steps, walk for a pre-determined period of time or distance, perform a specific exercise, exercise for a well-defined duration of time, or breathe according to a pre-determined sequence.

In another aspect, the sensor comprises computer code that operates algorithms configured to process: 1) the impedance plethysmogram to determine a first fiducial value and a SV value; 2) the ECG QRS complex to determine a second fiducial value; 3) the first and second fiducial values to determine a PAT value; and 4) the PAT to estimate a blood pressure value. For example, algorithms operating on the sensor can be configured to perform the following operations to measure physiological information from the patient: 1) take a mathematical derivative of the impedance plethysmogram; 2) determine a minimum or maximum value of the mathematical derivative; 3) estimate an area under the curve of the mathematical derivative; 4) determine a maximum value of the ECG QRS complex; 5) determine an inverse of the PAT value; 6) process the inverse of the PAT value with a linear or non-linear equation to estimate the blood pressure value; 7) process the impedance plethysmogram to estimate PP; 8) process the PP with a linear or non-linear equation to estimate SV; and 9) process PP along with PAT to estimate SBP or DBP.

The invention has many advantages. At a high level, the invention combines a sophisticated physiological sensor with conventional electronic/software systems (television, mobile device, video game) to help characterize CHF and other patients at home. The combination of these components potentially facilitates patient compliance and helps drive patients to: 1) better physiological monitoring with an effort to keep them out of the hospital; and 2) improve their condition by promoting better health.

BRIEF DESCRIPTION OF THE DRAWINGS

FIG. 4 shows a three-dimensional image of the sensor of FIG. 1, along with a close-up view of electronic components used for digital and power circuitry within the sensor;

FIG. 7A shows a schematic view of the sensor communicating through Bluetooth with the control unit, and the control unit communicating through infrared radiation with the television;

FIG. 7B shows a schematic view of the sensor simultaneously communicating through Bluetooth and infrared radiation with, respectively, the control unit and television;

DETAILED DESCRIPTION OF THE INVENTION

Figure 1:
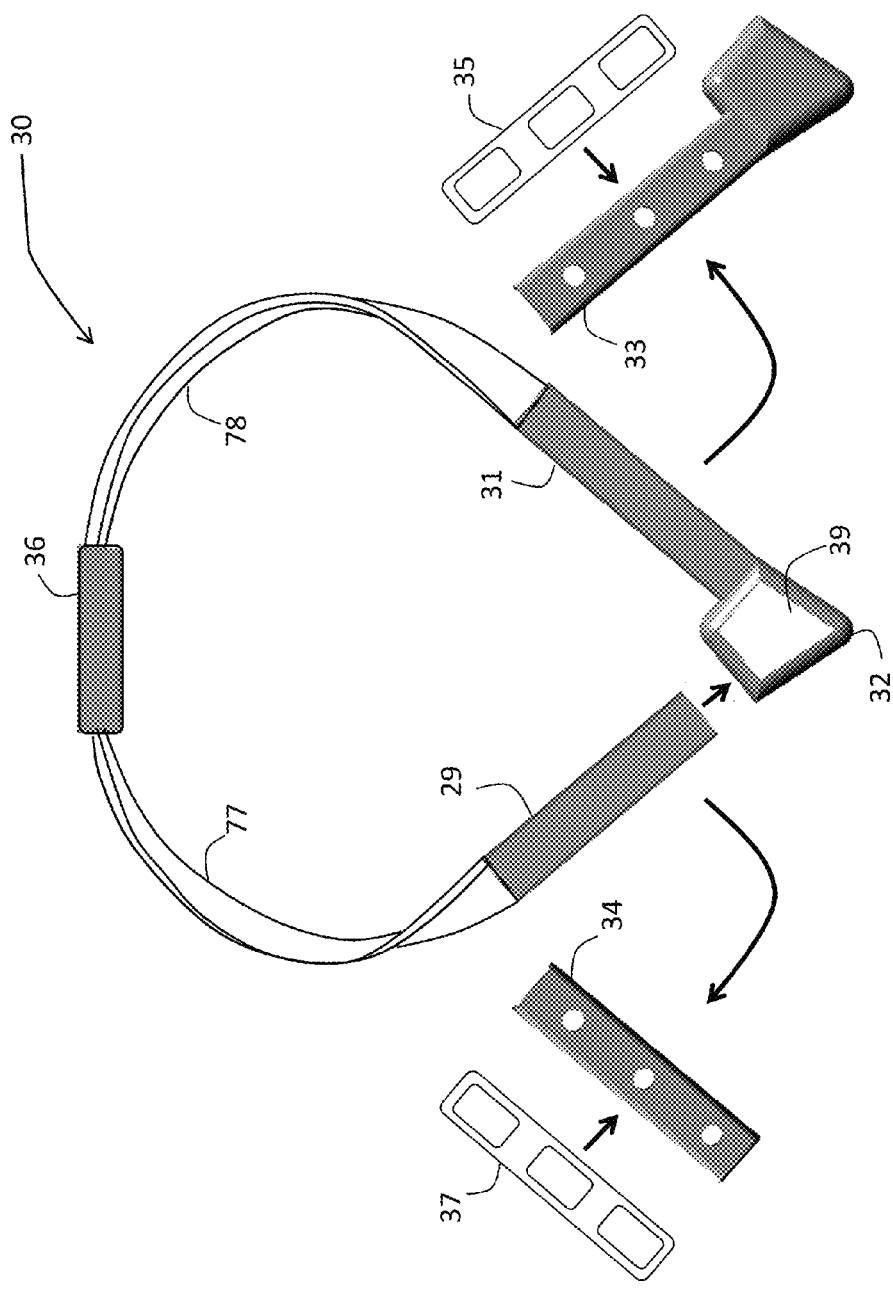
FIG. 1 shows a three-dimensional image of the sensor according to the invention that measures vital signs, hemodynamic parameters, and motion/posture/activity level from an ambulatory patient.

As described above, the sensor according to the invention provides a simple, easy-to-wear sensor that measures all vital signs (HR/PR, SpO2, RR, TEMP, and SBP/DBP), hemodynamic parameters (thoracic fluid levels, CO, SV), and motion-related parameters (posture, degree of motion, activity level, and falls). Perhaps the most complex measurement made by the necklace is that for blood pressure, i.e. SBP and DBP. These parameters are determined from a PAT separating heartbeat-induced pulses in the ECG and TBI waveforms, coupled with a PP determined from SV determined from the TBI waveform. Using these measurement systems, the necklace's measurement of SBP and DBP is both continuous and cuffless.

All analog and digital electronics associated with these measurements are integrated into the strands of the necklace. This means a single component, shaped like a piece of conventional jewelry as opposed to a bulky medical device, measures a robust set of parameters that can characterize a patient using both one-time and continuous measurements. Measurements can take place over just a few minutes or several hours, and are made in medical facilities and at home. The necklace includes a simple LED in its amulet to indicate high-level conditions (e.g., red/yellow/green illuminations depending on the patient's health, as determined from the vital signs and hemodynamic parameters). Also in the amulet is a battery that is easily replaced for long-term, continuous measurements. The necklace includes a wireless transmitter (operating Bluetooth and/or 802.11a/b/g/n) that sends data to, e.g., a conventional mobile device (e.g. cellular telephone, tablet computer, desktop/laptop computer, or plug-in hub).

During a measurement, three-part electrodes 35, 37 on the underside of right 31 and left 29 strands of the sensor 30 collect physiological signals, which a microprocessor, located within the strands, processes to determine the physiological information. Using a wireless (e.g. Bluetooth) transmitter also within its strands, the sensor 30 communicates directly with a conventional television set 100, as shown in detail in FIGS. 5 and 7, which then displays the physiological information along with other content, described in more detail below. In this way, the sensor 30 and television set 100 collectively function as an in-home system that uses conventional consumer items—i.e. something that resembles a piece of jewelry and a consumer electronics component—to measure the patient's vital signs. Other electronic items within the patient's home, such as a cable modem or wireless telephone, can transmit the physiological information to a web-based system. Thus clinicians remote from the patient's house, e.g. in a call center or hospital, can view the information and follow up with the patient by recommending changes in diet and exercise, with the goal of preventing hospitalization. In particular, the sensor 30 and television 100 can detect the early onset of CHF. Patients having this condition have a high rate of rehospitalization; however the disease can be predicted early on by a constellation of parameters, including weight gain, thoracic fluids, and changes in RR and HR. And control of these parameters, all of which are measured by the system and a complementary wireless weight scale, can prevent rehospitalization.

Because patients that have CHF are typically immobile and tend to watch television for extended periods of time, the system can potentially improve the patient's compliance for making important, daily measurements. For elderly patients, in particular, their existing television set may be preferable for displaying physiological information compared to a computer, mobile phone, or tablet, which typically have smaller display screens and thus may be difficult to view. As described above, patients frequently watch several hours of television each day, and periods used for commercials, etc., may be ideal times to make quick measurements of their physiological signals. In another embodiment, the system can render a graphical user interface that resembles a video game, which in turn can be entertaining to the patient. The combination of these factors may improve the patient's compliance.

Referring back to FIG. 1, the necklace-shaped sensor 30 is designed to comfortably drape around the patient's neck like a conventional piece of jewelry. Ideally the sensor 30 is worn for just one or more short periods of time each day, e.g. immediately before or after meals, for a period of about 10-15 minutes. Alternatively the patient may wear the sensor 30 continuously. The sensor 30 features three regions 29, 31, 36 that house rigid electronic components disposed on fiberglass circuit boards; two regions 77, 78 containing flexible circuits or wires connect these regions. Ideally a soft, flexible material, such as silicone rubber, encases all of the regions 29, 31, 36, 77, and 78 so that both comfort and mechanical stability are maximized. The motivation behind the design shown in FIG. 1 is to make use of the sensor as simple as possible, while making it look like something that the patient would potentially wear for non-medical applications.

Referring to FIGS. 1 and 4, the region 31 at one distal end of the sensor 30 features digital circuitry and a 'pendant' 32 housing a battery 81, light-emitting diode (LED) 82, and other circuit elements. A clear or translucent plastic window 39 protects these circuit elements while allowing radiation from the LED 82 to be visible. Additionally, the LED 82 may be an infrared LED that can be used as a remote control device to control the television set, as is shown in more detail in FIG. 7B. The pendant 32 also features a magnetically active connector 83. To make a measurement, the connector 83 connects to a magnet (not shown in the figure) with a circuit component in a region 29, which is in the opposing distal end of the sensor 30. The magnetically active connector 83 also includes a magnetic reed switch that moves to an 'on' position when the magnetically active connector 83 and the magnet are proximal to one another. This forms a continuous 'necklace' around the patient's neck. Stated another way, during use, the patient drapes the necklace-shaped sensor around their neck, and then brings the distal region 29 proximal to the pendant 32. This causes the magnet within the region 29 to snap next to the magnetically active connector 83 within the pendant 32. And this act, in turn, activates the reed switch, thus powering on the necklace. In doing this, the battery 81 within the pendant supplies power to all the electronic components of the necklace, thereby allowing it to measure physiological signals as described in more detail below. Electronic components within the region 31 that are powered by the battery 81 include a removable flash memory 89 for storing data that the sensor 30 measures, a Bluetooth transmitter 87 for transmitting these data to a remote receiver, and a digital circuit board 85 that houses data-processing components such as a microprocessor, memory, analog-to-digital converter, etc.

Figure 2:
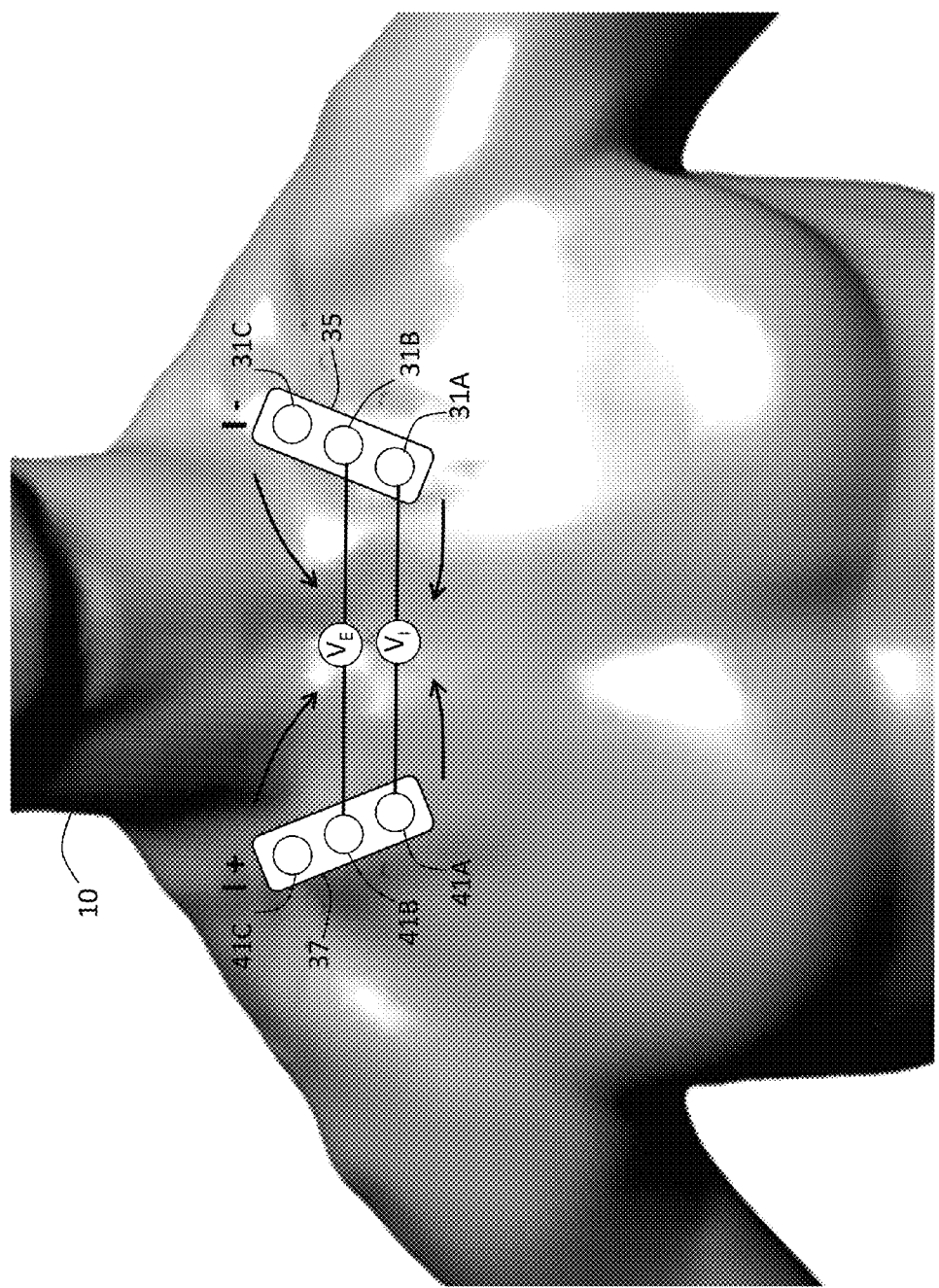
FIG. 2 shows a schematic drawing of electrodes used for the ECG and TBI measurements positioned on the patient's chest using the sensor of FIG. 1.

As shown in FIG. 1 and in more detail in FIG. 2, the sensor 30 measures physiological signals with a pair of 3-part electrodes 35, 37 that attach, respectively, to backing components 33, 34 located on the underside of regions 31, 29. The electrodes preferably feature magnetically active snaps that attach to magnets within the backing components 33, 34. The electrodes 35, 37 are described in detail in the following co-pending patent application, the contents of which are incorporated herein by reference: MAGNETICALLY CONNECTED ELECTRODE FOR MEASURING PHYSIOLOGICAL SIGNALS, U.S. Ser. No. 61/757,980, filed Jan. 29, 2013. In addition to measuring physiological signals, the electrodes 35, 37 hold the sensor 30 firmly in place near the patient's chest, thus reducing motion-related artifacts and improving the quality of signals measured from the patient.

Figure 10:
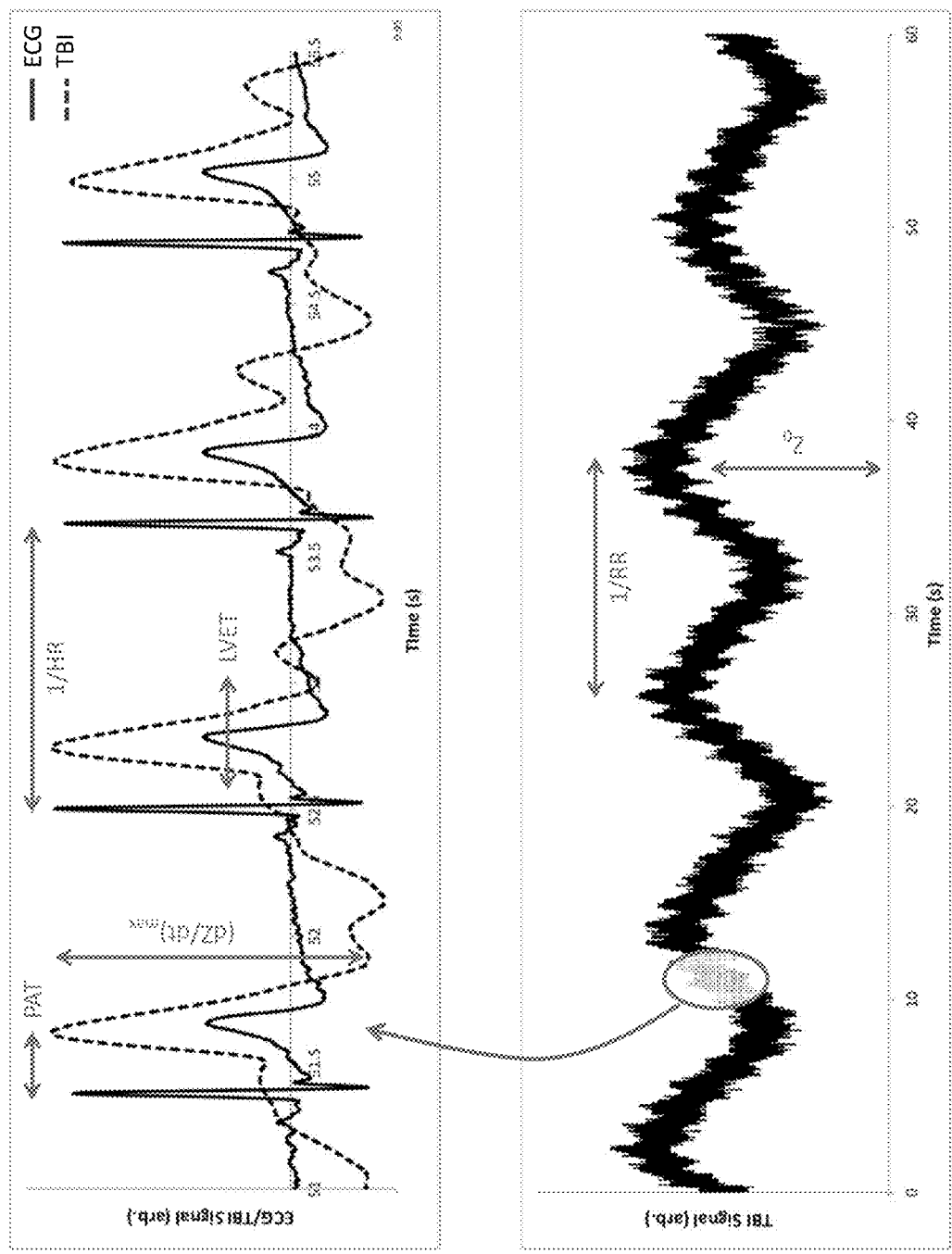
FIG. 10 shows time-dependent plots of ECG and TBI waveforms featuring heartbeat-induced pulses (top) and a TBI waveform showing breathing-induced oscillations (bottom), all measured with the sensor of FIG. 1.

As shown in FIG. 2, the sensor measures both ECG and TBI time-dependent waveforms. The microprocessor within the digital circuit board 85 processes these waveforms to determine HR, RR, thoracic fluid levels, CO, and SV as described in more detail below. Additionally, the following co-pending patent applications, the contents of which are incorporated herein by reference, describe in more detail algorithms for distilling these parameters from the time-dependent waveforms: NECKLACE-SHAPED PHYSIOLOGICAL MONITOR, U.S. Ser. No. 61/767,186, filed Feb. 20, 2013. FIG. 10 shows examples of the time-dependent waveforms and describes their origin; these are described in more detail below.

Figure 3:
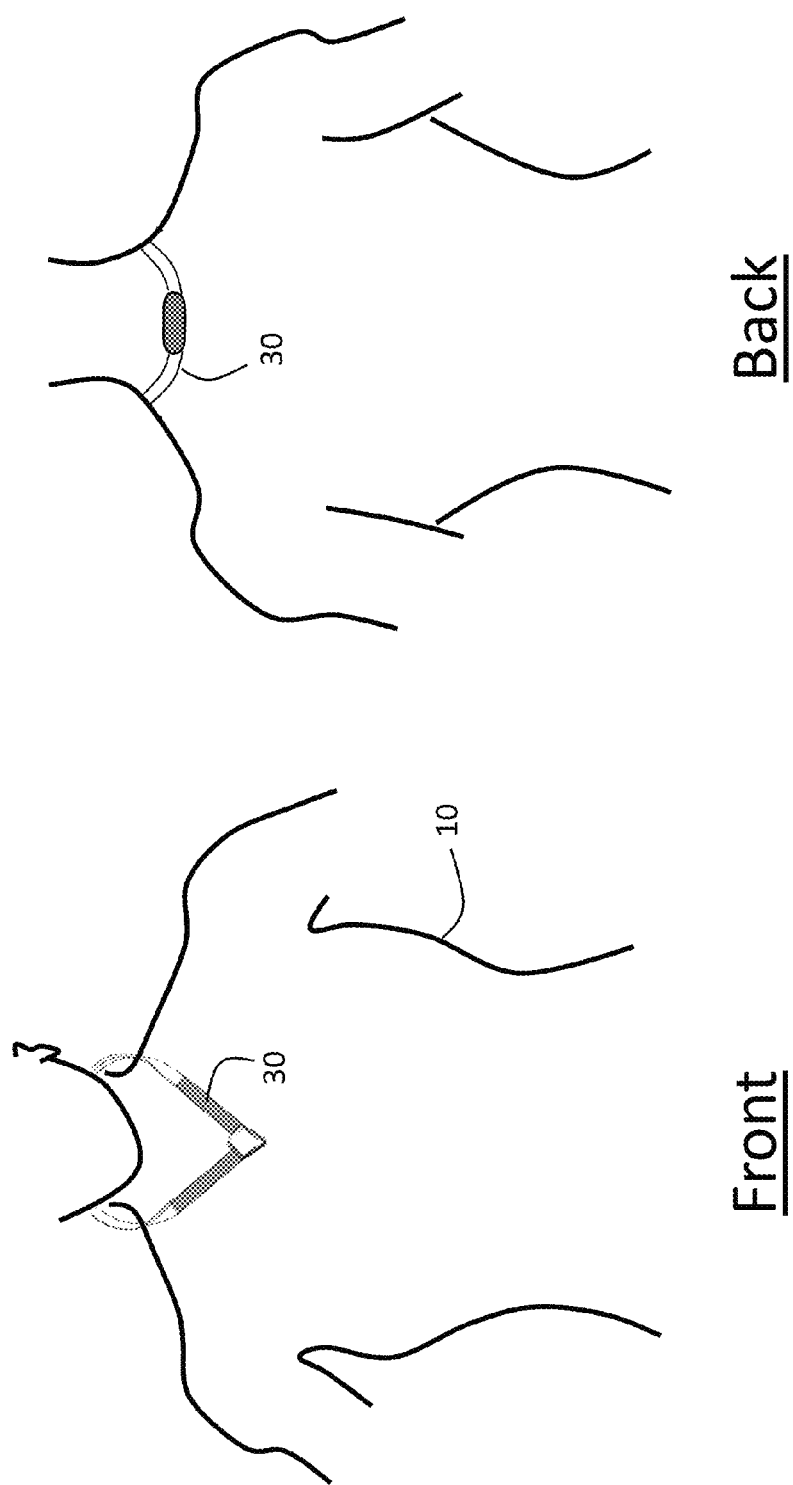
FIG. 3 shows schematic drawings of the front and back of a patient wearing the sensor of FIG. 1.

FIG. 3 indicates how the above-described electrode measures TBI waveforms and CO/SV values from a patient. As described above, 3-part electrode patches 35, 37 within the neck-worn sensor attach to the patient's chest. Ideally, each patch 35, 37 attaches just below the collarbone near the patient's left and right arms. During a measurement, the impedance circuit injects a high-frequency, low-amperage current (I) through outer electrodes 31C, 41C. Typically the modulation frequency is about 70 kHz, and the current is about 4 mA. The current injected by each electrode 31C, 41C is out of phase by 180°. It encounters static (i.e. time-independent) resistance from components such as bone, skin, and other tissue in the patient's chest. Additionally, blood and fluids in the chest conduct the current to some extent. Blood ejected from the left ventricle of the heart into the aorta, along with fluids accumulating in the chest, both provide a dynamic (i.e. time-dependent) resistance. The aorta is the largest artery passing blood out of the heart, and thus it has a dominant impact on the dynamic resistance; other vessels, such as the superior vena cava, will contribute in a minimal way to the dynamic resistance.

Inner electrodes 31A, 41A measure a time-dependent voltage (V) that varies with resistance (R) encountered by the injected current (I). This relationship is based on Ohm's Law, shown below in Eq. 3:

$$V = I \cdot R \tag{3}$$

During a measurement, the time-dependent voltage is filtered by the impedance circuit, and ultimately measured with an analog-to-digital converter within the electronics module. This voltage is then processed to calculate SV with an equation such as that shown below in Eq. 4, which is the Sramek-Bernstein equation, or a mathematical variation thereof. Historically parameters extracted from TBI signals are fed into the equation, shown below, which is based on a volumetric expansion model taken from the aortic artery:

$$SV = \delta \frac{L^3}{4.25} \frac{\left(\frac{dZ(t)}{dt}\right)_{max}}{Z_0} LVET \tag{4}$$

In Eq. 4, Z(t) represents the TBI waveform, δ represents compensation for body mass index, Zo is the base impedance, L is estimated from the distance separating the current-injecting and voltage-measuring electrodes on the thoracic cavity, and LVET is the left ventricular ejection time, which is the time separating the opening and closing of the aortic valve, and can be determined from the TBI waveform. Alternatively LVET can be calculated from the HR using an equation called 'Weissler's Regression', shown below in Eq. 5:

$$LVET = -0.0017 \times HR + 0.413 \tag{5}$$

Weissler's Regression allows LVET, to be estimated from HR determined from the ECG waveform. This equation and several mathematical derivatives, along with the parameters shown in Eq. 4, are described in detail in the following reference, the contents of which are incorporated herein by reference: '*Impedance Cardiography, Pulsatile blood flow and the biophysical and electrodynamic basis for the stroke volume equations*', Bernstein, *Journal of Electrical Bioimpedance*, Vol. 1, p. 2-17, 2010. Both the Sramek-Bernstein Equation and an earlier derivative of this, called the Kubicek Equation, feature a 'static component', $Z_0$, and a 'dynamic component', $\Delta Z(t)$, which relates to LVET and a $(dZ/dt)_{max}/Z_0$ value, calculated from the derivative of the raw TBI signal, Z(t). These equations assume that $(dZ(t)/dt)_{max}/Z_o$ represents a radial velocity (with units of Ω/s) of blood due to volume expansion of the aorta.

In Eq. 4 above, the parameter $Z_0$ will vary with fluid levels. Typically a high resistance (e.g. one above about 30Ω) indicates a dry, dehydrated state. Here, the lack of conducting thoracic fluids increases resistivity in the patient's chest. Conversely, a low resistance (e.g. one below about 19Ω) indicates the patient has more thoracic fluids, and is possibly overhydrated. In this case the abundance of conducting thoracic fluids decreases resistivity in the patient's chest. The TBI circuit and specific electrodes used for a measurement may affect these values. Thus, the values can be more refined by conducting a clinical study with a large number of subjects, preferably those in various states of CHF, and then empirically determining 'high' and 'low' resistance values.

FIG. 10 shows derivatized TBI and ECG waveforms measured with the necklace of FIG. 1 plotted over a short (about 5 seconds) time window (top), and TBI waveforms plotted over a longer window (bottom, 60 seconds). Referring first to the top portion of the figure, individual heartbeats produce time-dependent pulses in both the ECG and TBI waveforms. The TBI waveform shown in the figure is the first mathematical derivative of a raw TBI waveform. As is clear from the data, pulses in the ECG waveform precede those in the TBI waveform. The ECG pulses, each featuring a sharp, rapidly rising QRS complex, indicate initial electrical activity in contractions in the patient's heart, and, informally, the beginning of the cardiac cycle. The QRS complex is the peak of the ECG waveform. TBI pulses follow the QRS complex by about 100 ms, and indicate blood flow through arteries in the patient's thoracic cavity. These signals are dominated by contributions from the aorta, which is the largest artery in this region of the body. During a heartbeat, blood flows from the patient's left ventricle into the aorta. The volume of blood is the SV. Blood flow enlarges this vessel, which is typically very flexible, and also temporarily aligns blood cells (called erythrocytes) from their normally random orientation. Both of these mechanisms—enlargement of the aorta and temporary alignment of the erythrocytes—improve electrical conduction near the aorta, thus decreasing the electrical impedance as measured with TBI. The waveform shown in the upper portion of FIG. 10 is a first derivative of the raw TBI waveform, meaning its peak represents the point of maximum impedance change.

A variety of time-dependent parameters can be extracted from the ECG and TBI waveforms. For example, as shown in the upper portion of the figure, it is well know that HR can be determined from the time separating neighboring ECG QRS complexes. Likewise, LVET can be measured directly from the TBI pulse. LVET is measured from the onset of the derivatized pulse to the first positive going zero crossing. Also measured from the derivatized TBI pulse is $(dZ/dt)_{max}$, a parameter that is used to calculate SV, as shown in Eq. 4 and described in more detail in the reference described above.

The time difference between the ECG QRS complex and the peak of the derivatized TBI waveform represents a PAT. This value can be calculated from other fiducial points, particularly on the TBI waveform (such as the base or midway point of the heartbeat-induced pulse). But typically the peak of the derivatized waveform is used, as it is relatively easy to develop a software beat-picking algorithm that finds this fiducial point.

PAT correlates inversely to SBP and DBP, as shown below in Eqs. 6-7, where $m_{SBP}$ and $m_{DBP}$ are patient-specific slopes for, respectively, SBP and DBP, and $SBP_{cal}$ and $DBP_{cal}$ are values, respectively, of SBP and DBP measured during a calibration measurement. Without the calibration PAT only indicates relative changes in SBP and DBP. A calibration can be provided with conventional means, such as an oscillometric blood pressure cuff or in-dwelling arterial line. The calibration yields both the patient's immediate value of SBP and DBP. Multiple values of PAT and blood pressure can be collected and analyzed to determine patient-specific slopes $m_{SBP}$ and $m_{DBP}$, which relate changes in PAT with changes in SBP and DBP. The patient-specific slopes can also be determined using pre-determined values from a clinical study, and then combining these measurements with biometric parameters (e.g. age, gender, height, weight) collected during the clinical study.

$$SBP = \frac{m_{SBP}}{PTT} + SBP_{cal} \quad (6)$$

$$DBP = \frac{m_{DBP}}{PTT} + DBP_{cal} \quad (7)$$

In embodiments, waveforms like those shown in the upper portion of FIG. 10 are processed to determine PAT, which is then used to determine either SBP or DBP according to Eqs. 6 or 7. Typically PAT and SBP correlate better than PAT and DBP, and thus this parameter is first determined. Then PP is estimated from SV, calculation of which is described below. Most preferably, instant values of PP and SV are determined, respectively, from the blood pressure calibration and from the TBI waveform.

PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET). The slope can be estimated from a universal model that, in turn, is determined using a population study. Alternatively, a slope tailored to the individual patient is used. Such a slope can be selected, for example, using biometric parameters describing the patient, as described above. Here, PP/SV slopes corresponding to such biometric parameters are determined from a large population study, and then stored in computer memory on the necklace. When a necklace is assigned to a patient, their biometric data is entered into the system, e.g. using a mobile telephone that transmits the data to a microprocessor in the necklace via Bluetooth. Then an algorithm on the necklace processes the data and selects a patient-specific slope. Calculation of PP from SV is described in the following reference, the contents of which are incorporated herein by reference: 'Pressure-Flow Studies in Man. An Evaluation of the Duration of the Phases of Systole', Harley et al., Journal of Clinical Investigation, Vol. 48, p. 895-905, 1969. As described in this reference, the relationship between PP and SV for a given patient typically has a correlation coefficient (r) that is greater than 0.9, which indicates excellent agreement between these two properties. Similarly, in the above-mentioned reference, SV is shown to correlate with the product of PP and LVET, with most patients showing an r value of greater than 0.93, and the pooled correlation value (i.e. that for all subjects) being 0.77. This last result indicates that a single linear relationship between PP, SV, and LVET may hold for all patients.

More preferably, PP is determined from SV using relative changes in these values. Typically the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: 'Pulse pressure variation and stroke volume variation during increased intra-abdominal pressure: an experimental study', Didier et al., Critical Care, Vol. 15:R33, p. 1-9, 2011. Here, the relationship between PP variation and SV variation for 67 subjects displayed a linear correlation of r=0.93, and extremely high value for pooled results that indicates a single, linear relationship may hold for all patients.

From such a relationship, PP is determined from the TBI-based SV measurement, and SBP is determined from PAT. DBP is then calculated from SBP and PP.

The necklace determines RR from both the TBI waveform, and from a motion waveform generated by the accelerometer (called the ACC waveform), which is typically located in analog circuitry within the necklace, as described above. The bottom portion of FIG. 10 indicates how the TBI waveform yields RR. In this case, the patient's respiratory effort moves air in and out of the lungs, thus changing the impedance in the thoracic cavity. This time-dependent change maps onto the TBI waveform, typically in the form of oscillations or pulses that occur at a much lower frequency than the heartbeat-induced cardiac pulses shown in the upper part of FIG. 10. Simple signal processing (e.g. filtering, beat-picking) of the low-frequency, breathing-induced pulses in the waveform yields RR.

Likewise, the ACC waveform will reflect breathing-induced movements in the patient's chest. This results in pulses within the waveform that have a similar morphology to those shown in the lower portion of FIG. 10 for the TBI waveform. Such pulses can be processed as described above to estimate RR. RR determined from the ACC waveform can be used by itself, or processed collectively with RR determined from the TBI waveform (e.g., using adaptive filtering) to improve accuracy. Such an approach is described in the following patent application, the contents of which are incorporated herein by reference: BODY-WORN MONITOR FOR MEASURING RESPIRATION RATE, U.S.S.N 20110066062, Filed Sep. 14, 2009.

As shown in the lower portion of FIG. 10, the baseline of the TBI waveform, called Zo, can be easily determined. Zo is used to determine SV, as described above in Eq. 4.

Figure 5:
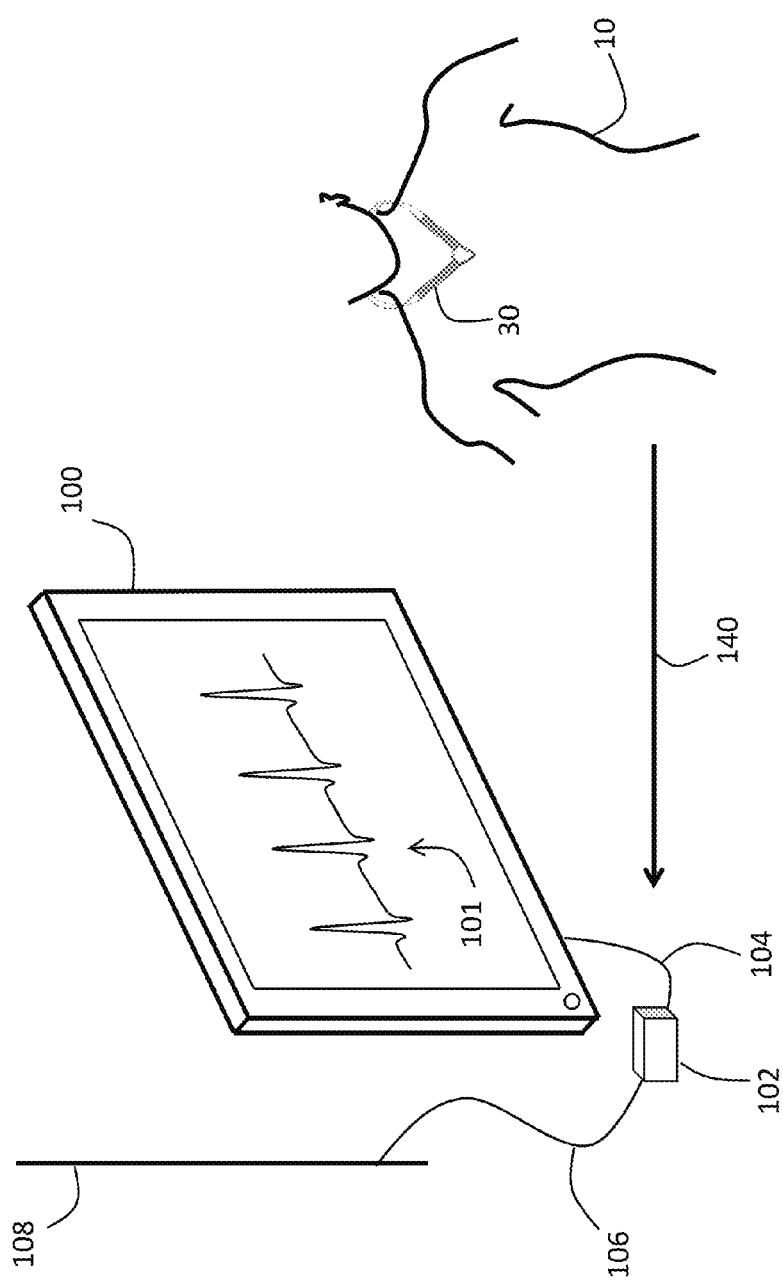
FIG. 5 shows a schematic view of the sensor of FIG. 1 wirelessly transmitting information for viewing on a conventional television.
Figure 6:
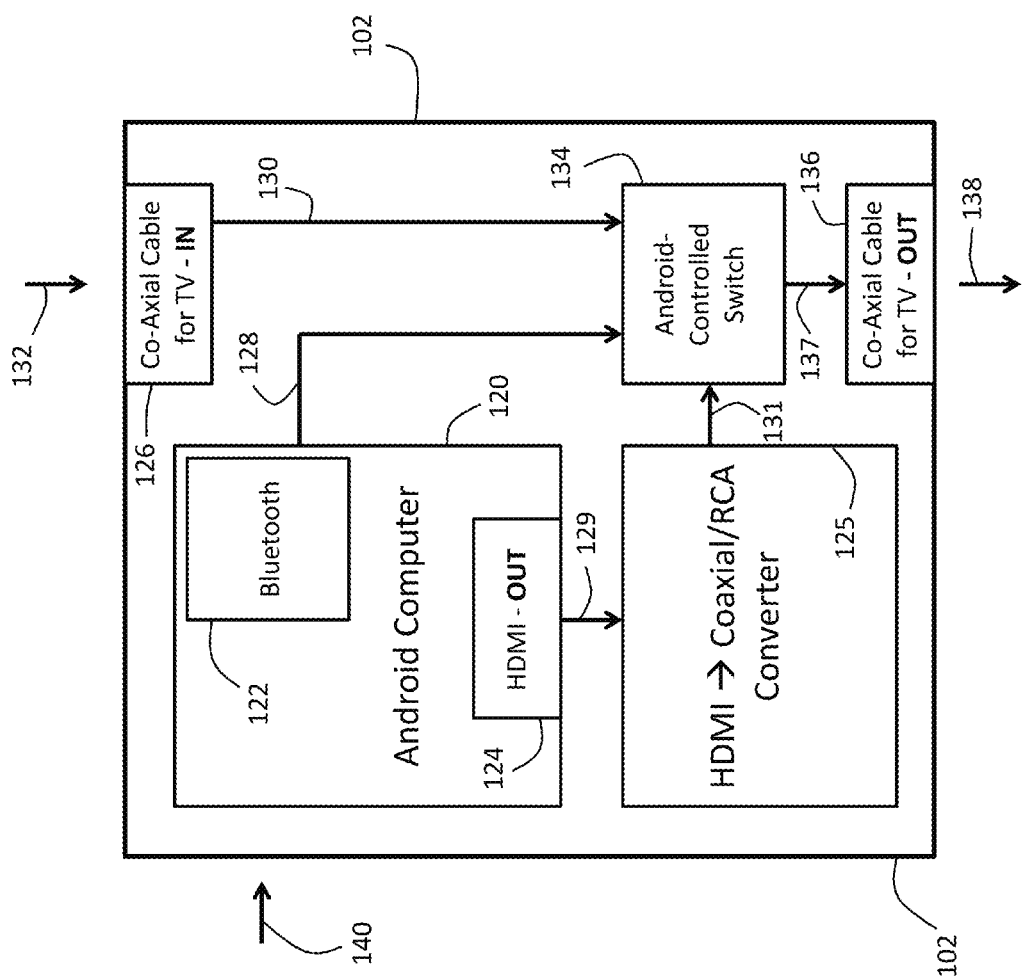
FIG. 6 shows a schematic view of a control unit used to integrate with the sensor and control the television of FIG. 5.
Figure 8B:
FIGS. 8A-D show photographs of different screens of a graphical user interface operating on a television set.
Figure 8D:
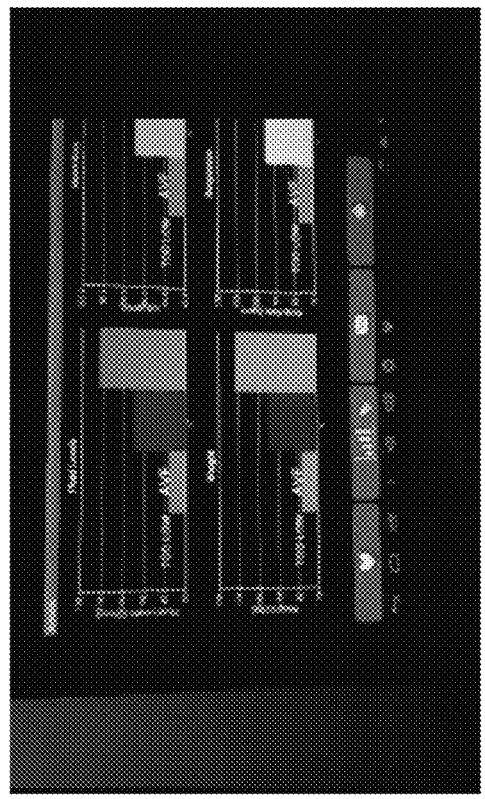
Figure 8A:
Figure 8C:

FIGS. 5-7 show how the sensor 30 attaches to the patient 10 and transmits information to a conventional television set 100. Referring first to FIGS. 5 and 6, as described above, in one embodiment a patient 10 wears the sensor 30 around their neck. Electrodes described in detail above measure signals that yield time-dependent ECG and TBI waveforms, which algorithms operating on a microprocessor within the sensor 30 process to generate physiological information, such as thoracic fluids, HR, RR, CO, SV, SYS, and DIA. The Bluetooth transceiver within the sensor 30 transmits both numerical and waveform data to a receiver module 102, as indicated by the arrow 140. FIG. 6 shows electronic components within the receiver module 102 in more detail. More specifically, in preferred embodiments it includes a single-board Android computer 120, which typically features an Arm Cortex processor running the Android operating system. The Android computer 120 also includes a Bluetooth module 122, which receives control signals from the sensor 30 as indicated by the arrow 140. The control signals, for example, indicate that the patient 10 is wearing the sensor 30, and activate the Android computer 120 and control its associated IO pints.

Figure 9:
FIG. 9 shows a photograph of a single screen of the graphical user interface operating on a tablet computer.

The purpose of the receiver module 102 is to render an Android software application on the television screen while posing minimal imposition to the patient. A graphical user interface associated with the software application is shown in FIGS. 8A-D (for a television) and FIG. 9 (for a tablet computer). More specifically, with the receiver module 102 it is not necessary for the patient to perform complicated functions with their standard remote control, such as changing the video source for the television 100. Instead, the Bluetooth receiver 122 within the Android computer 120 receives the control signals sent from the sensor 30 that indicate the patient is wearing the device, and that it is ready to send information. Once the control signals are received, the Android computer 120 processes them and, in response, activates an Android-controlled switch 134 within the receive module 102 by sending signals through line 128. IO lines from the Android computer 120, for example, control the switch 134. During its normal state, the switch 134 passes signals from a standard co-axial cable that enter the receiver module 102, as indicated by arrow 132, through an incoming connector 126. For example, the incoming connector 126 may be a standard co-axial connector that receives television signals from a standard cable box in the patient's home. These signals pass along line 130 in the receiver module 102. In the absence of any control signals, the switch 134 simply passes the television signals that propagate along lines 130 and 137 to an outgoing connector 136, which then passes them as indicated by arrow 138 to the television, where they render standard programming. However, when the patient wears the necklace, the Bluetooth receiver 122 receives control signals, which pass along line 128 to the switch 134. The control signals activate the switch 134 so that it does not pass standard television signals that propagate along line 130, but instead passes signals for the Android application, which are generated by an HDMI→co-axial/RCA converter 125. More specifically, in the presence of control signals, the Android computer 120 launches the Android software application, the signals for which typically pass through a standard HDMI connector 124, as indicated by arrow 129. The converter 125 receives the signals and converts them to either coaxial or RCA signals, which then pass through a line indicated by arrow 131 to the switch 134. This component is now directed to pass the signals corresponding to the Android software application along a line indicated by arrow 137 to the outgoing connector 136, which then passes these signals to the television as indicated by arrow 138. The Android software application, screens of which are shown in FIGS. 8 and 9, renders a variety of content 101 on the patient's television 100, or alternatively a computer (e.g. desktop, laptop, or tablet computer) or mobile device (e.g. cellular telephone). The content, for example, can include numerical values, time-dependent waveforms, graphical images, and questionnaires directed at elucidating lifestyle and diet choices made by the patient that might indicate the onset of CHF.

In embodiments, the software application may guide the patient's through a pre-determined exercise routine while simultaneously collecting physiological information related to the patient's condition. For example, the software application may instruct the patient to take a number of steps while collecting motion signals indicating the number of steps, and ECG and impedance signals that indicate one or more of the following parameters: HR, RR, SV, CO, pulse transit time, and SBP/DBP estimated from pulse transit time. The Android computer described above can store these data, and evaluate them over time. This serves two purposes: 1) the data can be used to estimate improvements of declination in the patient's condition; and 2) exercise over time can actually improve the patient's condition. In one embodiment, for example, the Android computer operates a graphical user interface that resembles a conventional video game. The interface can guide the patient through a pre-determined exercise routine, monitor their progress relative to the pre-determined routine, and store physiological information along the way. The interface can be established so that both the patient and secondary users (e.g. select members of their family, friends, and medical professionals) can view the data. Preferably the interface displays the data in a time-dependent format so that trends are apparent. In this way, the secondary users can keep track of the patient, and the patient can leverage the power of social media websites (e.g. www.facebook.com) that allow information to be shared and processed by large groups of people.

In a related embodiment, algorithms operating on the Android computer can evaluate data collected during the pre-determined exercise routine to determine if the patient is entering heart failure. In particular, algorithms operating on the computer can process parameters related to SV, CO, and HR to determine this condition. Such algorithms are described in the following publication, the contents of which are incorporated herein by reference: 'Exercise and Heart Failure: A Statement From the American Heart Association Committee on Exercise, Rehabilitation, and Prevention', Pina et al., *Circulation, Vol.* 107, p. 1210-1225, 2003. Similarly, algorithms operating on the computer can process the product of CO and mean arterial pressure, called 'cardiac power', to determine how close the patient is to heart failure. Some approaches measure cardiac power after the patient walks for a pre-determined period of time (e.g. 6 minutes). Such algorithms are described in the following publication, the contents of which are incorporated herein by reference: 'Physiological range of peak cardiac power output in healthy adults', Bromley et al., Clin Physiol Funct Imaging, Vol. 26, p. 240-246, 2006.

When the necklace completes its measurements, the Bluetooth transceiver 122 receives control signals indicating this is the case, and instructs the Android computer 120 to terminate the software application, and restores the switch's state to one that passes conventional television signals. In this case, the incoming connector 126 receives incoming signals from the cable hookup, which then pass through the switch 134, lines 130 and 137, through the outgoing connector 136, and from there to the television 100.

With this system, the patient 10 only needs to put on the sensor 30, and never needs to operate any complicated buttons on their remote.

In embodiments, the Android computer 120 automatically launches the software application described above when the user wears the sensor. Alternatively, the computer 120 can launch the application at pre-determined times (e.g. right before or after meals) to force the patient into compliance. In still other embodiments, the patient wears the sensor continuously, and the computer launches the application when their physiological parameters meet pre-determined threshold values, e.g. high or low values. For patients that require continuous monitoring, the computer can exclusively operate the software application, i.e. it never passes conventional television signals. Other embodiments, of course, are within the scope of the invention.

FIGS. 7A and 7B, for example, show a few of these alternate embodiments. As shown in FIG. 7A, in one embodiment the receiver module 103A receives control signals via Bluetooth, as indicated by arrow 140. In this case the receiver module 103A features an infrared LED that illuminates optical signals in a manner similar to the remote control associated with the television 100, as indicated by arrow 142A. An infrared receiver 147 within the television receives the optical signals, and in response switches the video input in the television to receive the Android software application. This runs on an Android computer within the receiver module, as described above, and is ported to the television through a cable 146. In response the television renders a software application 101 on the television. When the measurements are complete, the receiver module 103A transmits a new set of optical signals to the infrared receiver 147 within the television. These instruct the television to switch back to standard programming, which it receives from a cable 144 emanating from the wall.

As shown in FIG. 7B, in yet another embodiment, the sensor 30 sends both Bluetooth control signals (indicated by arrow 140) to launch the Android software application 101 on the television, and infrared optical signals (indicated by arrow 142B) to control the television set. An LED in the sensor's pendant (similar to component 82 in FIG. 4) generates the infrared optical signals. These are used in a manner similar to that described above to render both the Android software application 101 and conventional programming on the television set 100.

In all of the above examples, the Android operating system is used to run the computer within the receiver module. This is preferred, primarily because of the low cost and the relative ease in writing software that runs on it. Of course, other operating systems and associated hardware platforms can also be used. These include the Microsoft's Windows operating system, Apple's IOS operating system, Linux, Micrium OS2, and basically any other operating system. Computer code used to write the Android software application can be based on any programming language, e.g. Java, C, C++, or programming environments based on these languages. For example, the graphical user interface 150 shown in FIGS. 8A-D and FIG. 9 is rendered using software written in a programming environment based on Java. As is shown in the figure, the interface 150 operates on a conventional television interface with an Android computer, and renders numerical data (e.g. thoracic fluids, heart rate, respiratory rate, weight detected from a weight scale, and body temperature) in an easy-to-read format.

Still other embodiments are within the scope of the following claims.

What is claimed is:

1. A system for monitoring a patient, comprising:
   a sensor configured to drape around the patient's neck, the sensor comprising an impedance sensor for measuring fluids in the patient, an ECG sensor for measuring cardiac activity corresponding to the patient, and a first wireless transceiver for transmitting information related to fluids and cardiac activity associated with the patient;
   a computer comprising a second wireless transceiver, video output system, and a CPU, the second wireless transceiver configured to receive control signals from the first wireless transceiver that control a software program operating on the CPU, and the CPU configured to render a graphical user interface that displays the information transmitted from the sensor through the video output system; and
   a mobile device that interfaces to the computer through the video output system and renders the graphical user interface.

2. The system of claim 1, wherein the sensor is configured to send control signals to the CPU configured to activate the software program.

3. The system of claim 2, wherein the control signals power on the CPU.

4. The system of claim 2, wherein the control signals activate IO pins in the CPU.

5. The system of claim 1, wherein the CPU operates a second software program that automatically launches the graphical user interface on the mobile device.

6. The system of claim 5, wherein the CPU is configured to automatically launch the software program at a pre-determined time.

7. The system of claim 1, wherein the CPU operates a second software program that launches the graphical user interface when it detects that the patient has been operating their mobile device for a predetermined period of time.

8. The system of claim 1, wherein the sensor comprises a motion sensor.

9. The system of claim 8, wherein the motion sensor is an accelerometer.

10. The system of claim 8, wherein the CPU operates a second software program that launches the graphical user interface when the motion sensor detects that the patient has been sedentary for a pre-determined period of time.

11. The system of claim 8, wherein the CPU operates a second software program that launches the graphical user interface when the motion sensor detects that the patient is in motion.

12. The system of claim 1, wherein the CPU operates a second software program that launches the graphical user interface so that it interrupts graphical content displayed on the mobile device.

13. The system of claim 12, wherein the CPU operates a second software program that launches the graphical user interface so that it is displayed on a web page rendered on the mobile device.

14. The system of claim 1, wherein the ECG sensor measures a heart rate from the patient.

15. The system of claim 14, wherein the CPU operates a second software program that launches the graphical user interface when the heart rate exceeds a predetermined value.

16. The system of claim 14, wherein the ECG sensor measures a heart rate variability from the patient.

17. The system of claim 16, wherein the CPU operates a second software program that launches the graphical user interface when the heart rate variability exceeds a predetermined value.

18. The system of claim 1, wherein the impedance sensor measures a level of fluids from the patient.

19. The system of claim 18, wherein the CPU operates a second software program that launches the graphical user interface when the level of fluids exceeds a predetermined value.

* * * * *